United States Patent [19]
Dugan

[11] Patent Number: 5,851,173
[45] Date of Patent: Dec. 22, 1998

[54] SELF SECURING BRACHY TUBE CAP

[75] Inventor: Harold Dugan, Milton, N.Y.

[73] Assignee: Marlene H. Dugan, Milton, N.Y.

[21] Appl. No.: 819,603

[22] Filed: Mar. 17, 1997

[51] Int. Cl.⁶ ..................................................... A61N 5/00
[52] U.S. Cl. ........................ 600/7; 600/1; 600/3; 604/93
[58] Field of Search ................................ 604/93; 600/1, 600/3, 7

[56] References Cited

U.S. PATENT DOCUMENTS 5,141,487  8/1992  Liprie ........................................... 600/7
5,242,373  9/1993  Scott et al. .................................. 600/7

Primary Examiner—John D. Yasko
Attorney, Agent, or Firm—Joseph L. Spiegel

[57] ABSTRACT

A soft plastic Brachy tube cap has a tubular body with one closed and one open end. The body's internal bore is sized so that the end of a Brachy tube fits snugly within the body when inserted through the open end. A pair of spaced locking rings integral with the body are adapted to fit about the Brachy tube. If the cap receives pressure towards removal, the two rings deform, through the pressure on the connecting straps, which results in reducing the bore radius and causes them to bend tighter on the Brachy tube. This prevents displacement of the caps.

2 Claims, 1 Drawing Sheet

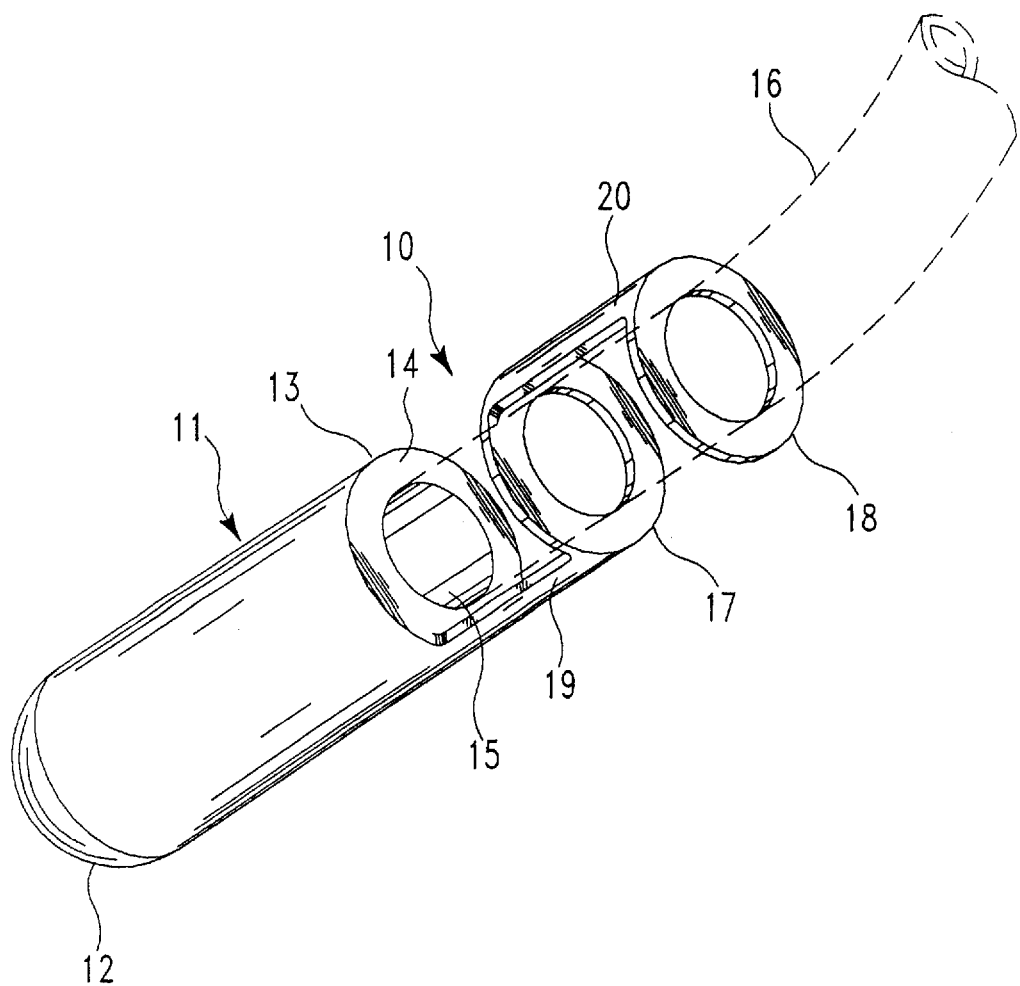

SELF SECURING BRACHY TUBE CAP

BACKGROUND OF INVENTION

1. Field of Invention

The present invention relates generally to the field of radiology and, in particular, to Brachy therapy. In Brachy therapy, a tube is introduced into a cancerous area of the body, as, for example, in treating breast and prostate cancer. A seed of radioactive material such as iridium is inserted into the tube and moved periodically in incremental steps along the length of the tube.

In the past these Brachy tubes, while sealed at the end first introduced into the body, are open at the externally exposed end of the tube. The open end is where the physician gains access to the interior or bore of the tube, for internal initial and step movement of the seed along the tube.

After the physician has gained necessary access to the interior of the tube, the open end of the tube, in the past, has been sealed after each treatment with gauze and tape.

There are various problems with the use of gauze and tape for closing the tube end. One is the amount of time required to close the ends of the tube with the gauze and tape after each treatment. Another problem is that the gauze and tape fall away from the end of the tube leaving its interior exposed. Water may then be introduced into the interior of the tube giving rise to hydraulic block which would alter the pre-set calibration regarding the path and duration of seed insertion.

Also, with this type of closure, a patient is ill-advised to shower due to the danger of introducing water into the tube.

Current and prior techniques for preventing water or other contaminants from entering Brachy tubes when inserted in the body of a patient are less than effective. It is to a solution to this problem to which the present invention is directed.

2. Description of the Prior Art

In the U.S. Pat. No. to Farjas, 839,061, a sheet of paper coated with radioactive material is placed within a cylinder open at an end which is capped with a screw plug.

Harris, U.S. Pat. No. 1,603,767 discloses a radioactive material applicator in the form of a suppository with a mass of radioactive material disposed in the bore of the suppository body at its head and a removable plug closing the bore at its bottom.

Koff, U.S. Pat. No. 2,707,471 pertains to a surgical appliance for insertion in body openings comprising a tubular body, flexible at a closed end and rigid at its opposite end and closed by a cap threadedly secured thereto.

Rush, U.S. Pat. No. 3,060,924 relates to apparatus for application of radioactive material. The apparatus includes a bored tubular tandem for carrying an appropriate dosage of the material, closed at its proximate end and closed by a threaded cap at its opposite end.

Billingsley, U.S. Pat. No. 3,224,432, describes a cylindrically shaped device for irradiating a body cavity that utilizes radioactive pellets.

In Parsons, U.S. Pat. No. 4,2255,790, radioactive material is drawn through a guide tube from a storage position to a usage position on the end of a drive cable.

In van't Hooft, et al, U.S. Pat. No. 4,861,520, a drivable radioactive source capsule with a plug having an elongated closure portion is illustrated.

None of the foregoing references deals with the problem of closing the open end of externally exposed Brachy tubes.

SUMMARY OF INVENTION

An object of the invention is the provision of a cap for a Brachy tube which is easy to install and remove.

Another object is such a cap which prevents contaminants and water lock within the tube at all times, even during a patient's showering or bathing.

These and other objects, features and advantages of the invention are accomplished in accordance with the teachings of the present invention, one illustrative embodiment of which comprises a soft plastic Brachy tube cap having a tubular body with one closed and one open end. The body's intended bore is sized so that the end of a Brachy tube fits snugly within the body when inserted through the open end. A pair of spaced locking rings integral with the body are adapted to fit about the Brachy tube. If the cap receives pressure towards removal, the two rings deform, through the pressure on the connecting straps, which results in reducing the bore radius and causes them to bend tighter on the Brachy tube. This prevents displacement of the caps.

BRIEF DESCRIPTION OF DRAWINGS

Other objects, features and advantages of the present invention will be apparent from the accompanying drawing which is a perspective view of a novel Brachy tube cap constructed in accordance with the teachings of the present invention.

DESCRIPTION OF THE PREFERRED EMBODIMENT

Referring now to the drawing, the novel Brachy tube cap 10 of the present invention is made entirely of a soft plastic material such as a soft plastic vinyl resistent to solvents found in a clinical setting. The body 10 is typically 18 mm. in length and 5 mm. in diameter.

It is seen as including a tubular body 11 having closed end portion 12 and open end portion 13. End portion 13 has an outer circular surface 14. The body 11 has an internal bore 15, typically 2 mm., sized so that the end of a Brachy tube 16 when inserted through the open end portion 13 fits snugly within the body 11. The Brachy tube 16 is typically 14 to 16 inches long.

Cap 10 further includes first 17 and second 18 locking rings integral with tubular body 11 and adapted to fit snugly about the Brachy tube 16. Two locking caps are required to enable them to remain in an angular position relative to the Brachy tube. The two rings are codependent in maintaining their off-set position relative to the perpendicular aspect of the tube. The inside diameter of the rings is the same as the outside diameter of the Brachy tube. The material being used is elastic which allows for the snug fit.

Typically rings are 1 mm. thick. This thickness allows the flexibility necessary for them to perform their function and yet to maintain their strength and integrity for the full course of patient treatments. If thicker, they could damage the Brachy tube. If thinner they would deflect too much and lose the friction necessary to maintain the cap upon the tube.

A first strap 19 joins the lower edge of the open end 13 to the lower edge of the first locking ring 17. A second strap 20 joins the upper edge of ring 17 to the upper edge of ring 18. The position of straps 19 and 20 are alternated between top and bottom to allow both rings to be pulled into their respective angular positions thereby reducing their bore radius upon the Brachy tube. In the embodiment depicted, the straps are between 4 and 6 mm. to be able to maintain the locking rings in their position. If longer, there would be too much movement of the rings and would negate their function. If shorter, the straps will not allow the rings to achieve the deflection necessary to enter a locking mode.

The functioning of the cap is readily apparent. In use the cap 10 is installed on the end of the Brachy tube 16 with the locking rings being first slipped onto the tube. The cap is pushed onto the tube with the locking rings 17, 18 being pulled as far as possible along the tube 16.

If the cap 10 receives pressure towards removal, the two rings deform, through the pressure on the connecting straps 19, 20, which results in reducing the bore radius and causes them to bend tighter on the Brachy tube. This prevents displacement of the caps.

To remove the cap from the Brachy tube the locking rings 17, 18 are pushed towards the end of the tube 16, continuing until the cap is displaced.

The cap is removed before each treatment. In between treatments the cap remains on the exposed end of the Brachy tube which remains within the patient.

The cap prevents the introduction of water and other contaminants into the Brachy tube and allows the patient to shower and bathe.

The cap may easily and instantly be installed and removed saving considerable time for medical personnel and provide a more sterile environment. The cap also serves to protect the end of the Brachy tube from damage.

Tape adhesion to the tube as with prior art use of gauze and tape is eliminated.

It should be obvious that changes, additions and omissions may be made in the details and arrangement of parts without departing from the scope of the invention as defined in the appended claims.

What is claimed is:

1. A soft plastic Brachy tube cap comprising:

a tubular body with an internal base sized so that the end of a Brachy tube fits snugly within; and a pair of spaced locking rings integral with the tubular body and adapted to fit about the Brachy tube.

2. A soft plastic Brachy tube cap comprising:

a tubular body having a closed end position, an open end portion with an outer circular surface with upper and lower edges, and an internal base sized so that the end of a Brachy tube fits snugly within the body when inserted through the open end portion of the body;

first and second locking rings integral with the tubular body and adapted to fit about the Brachy tube, each ring having an upper and lower edge;

a first strap joining the lower edge of the open end circular position to the lower edge of the first ring; and a second strap joining the upper edge of the first ring to the upper edge of the second ring.

* * * * *